(12) United States Patent
Biehl

(10) Patent No.: US 6,425,899 B1
(45) Date of Patent: Jul. 30, 2002

(54) OBSTETRIC FORCEPS

(75) Inventor: Margit Biehl, St. Wendel (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/889,042

(22) PCT Filed: Jan. 12, 2000

(86) PCT No.: PCT/EP00/00164

§ 371 (c)(1),
(2), (4) Date: Oct. 24, 2001

(87) PCT Pub. No.: WO00/41634

PCT Pub. Date: Jul. 20, 2000

(30) Foreign Application Priority Data

Jan. 12, 1999 (DE) ............................. 199 00 795

(51) Int. Cl.[7] ............................................. A61B 17/42
(52) U.S. Cl. .................... 606/122; 606/119; 606/205
(58) Field of Search ................... 606/119, 121, 606/122, 123, 124, 125, 126, 127, 205; 604/74

(56) References Cited

U.S. PATENT DOCUMENTS

| | | | | |
|---|---|---|---|---|
| 2,637,230 A | | 5/1953 | Tinnerman et al. .......... 81/3 |
| 2,637,320 A | * | 5/1953 | Greenberg | |
| 3,785,381 A | | 1/1974 | Lower et al. ........... 128/323 |
| 5,578,043 A | * | 11/1996 | Galstian | |
| 5,649,934 A | * | 7/1997 | Smeltzer, III et al. | |

FOREIGN PATENT DOCUMENTS

DE 4235442 10/1992 ........... A61B17/44

* cited by examiner

*Primary Examiner*—Pedro Philogene
(74) *Attorney, Agent, or Firm*—Antonelli, Terry, Stout & Kraus, LLP

(57) ABSTRACT

Disclosed is an obstetric forceps for grasping a baby during childbirth, the forceps having blades which are approximately adapted to the shape of a baby's head, are made of a rigid material and have contact surfaces for grasping the baby's head, the contact surfaces being provided with at least one device for detecting the pressure prevailing between the contact surfaces and the baby's head. The invention is distinguished by the contact surfaces of the forceps blades each is provided with an elongated, elastically ductile contact body, and the pressure detection device is designed in such a manner that the contact body has, at least at the side facing the contact surface, an electrically conductive surface and that electrodes, which are insulated from each other, are provided at the contact surfaces of the forceps blades, upon deformation of the contact body, the electrodes being contactable with the same in such a manner that with increasing deformation of the contact body, an increasing number of electrodes are electrically interconnected by the electrically conductive surface of the contact body.

13 Claims, 2 Drawing Sheets

OBSTETRIC FORCEPS

TECHNICAL FIELD

The present invention relates to an obstetric forceps for grasping a baby during childbirth, which forceps have blades which are approximately adapted to the shape of a baby's head, are made of a rigid material and have contact surfaces for grasping the baby's head, which contact surfaces are provided with at least one device for detecting the pressure prevailing between the contact surface and the baby's head.

STATE OF THE ART

Obstetric forceps for grasping a baby during childbirth are common knowledge. Obstetric forceps are partly made of metal and comprise two forceps elements moveably connected by means of a joint, also referred to as a catch. State of the art forceps have a handle section and a grasping section which are separated by the joint. Forceps blades adapted to the shape of a baby's head are provided at the grasping section with which the baby's head can be grasped by exactly fitting around the head respectively at least partially surrounding the head. The handle section is provided with handles for operating the forceps. At the section leading to the joint of each handle, there is a laterally projecting extraction hook which is employed to extract the child grasped by the forceps out of the mother's body.

However, occasionally in so-called forceps births there is injury to the baby's head ranging from nerve damage to impression fractures of the skull caused by too much pressure applied by the forceps on the baby's head during delivery. The pressure acting on the baby's head cannot be controlled by means of known methods and devices. Thus, the pressure is solely controlled by the sensitivity of the fingers of the obstetrician operating the forceps. This can lead to problems particularly if the obstetrician is strong or inexperienced, because too much pressing force may be applied to the baby's head with such forceps.

Moreover, frequently the obstetric forceps touches the head only at certain points as the shape of a baby's head varies strongly and sometimes there are great radii of curvature. Therefore, the obstetric forceps does not always fit exactly around the baby's head. Thus, the force applied at the forceps handle may apply quite varying point pressures to the baby's head depending on to what degree the shape of the baby's head concurs with the shape of the forceps. If the forceps touches only a few, small points, more pressure is applied than if the forceps touches the baby's head at several points distributed over a large area.

In order to significantly reduce such head injuries to babies delivered with forceps, U.S. Pat. No. 2,637,230 describes an obstetric forceps in which the blades of the forceps are surrounded by an expandable, elastic volume that can be filled with compressed air and widened to largely surround the baby's head fitting snugly without coming into direct contact with the, usually metal, blades of the forceps.

However, the known obstetric forceps do not allow the physician to determine whether the presently applied pressing force between the forceps blades and the baby's head exceeds a predetermined maximum load. A remedy is the obstetric forceps of US printed publication U.S. Pat. No. 3,785,381 which is provided with a pressure sensor at the insides of the forceps blades facing the baby's head. This sensor indicates to the physician the currently prevailing pressing force at the site of the pressure-measuring sensor via a corresponding display device.

However, the known obstetric forceps provided with such pressure sensors have the drawback that the area where the pressure is measured is very restricted locally so that the physician is unable to prevent excessive pressure which may occur due to the blades of the forceps at sites not provided with pressure-measuring sensors.

DE 42 35 442 A1 describes an obstetric forceps whose blades are provided with a covering surrounding a cavity. This covering is fillable with a liquid or gaseous medium. The covering, which is preferably made of an expandable, elastic material, serves as a buffer cushion when the head is grasped and helps prevent local pressure peaks on the baby's head as far as possible. Moreover, a pressure sensor connected with the medium to which the pressure is applied permits determining the surface pressure between the obstetric forceps and the baby's head. However, this mode does not permit site-resolved detection of locally occurring pressure peaks.

DESCRIPTION OF THE INVENTION

The object of the present invention is to improve an obstetric forceps for grasping a baby's head during delivery, which forceps have blades, which are approximately adapted to the shape of a baby's head, are made of a rigid material and have contact surfaces for grasping the baby's head, which contact surfaces are provided with at least one device for detecting the pressure prevailing between the contact surface and the baby's head, in such a manner that an injury to the baby's head due to excessive local pressure is largely ruled out. It should, in particular, be possible for the physician to gently grasp the baby's head over a large surface and determine information, preferably site-resolved, about any possible excessive pressure that may occur over the entire contact area between the obstetric forceps and the baby's head.

The solution to the object of the present invention is set forth in claim 1. Advantageous further-developing features of the inventive idea are the subject matter of the subclaims and are described in the accompanying drawings with respective descriptions.

The invented obstetric forceps for grasping a baby during childbirth, which forceps have blades which are approximately adapted to the shape of a baby's head, are made of a rigid material and have contact surfaces for grasping the baby's head, which contact surfaces are provided with at least one device for detecting the pressure prevailing between the contact surface and the baby's head, is distinguished by the contact surfaces of the blades of the forceps being provided with an elongated, elastically ductile contact body and by the pressure detecting device being designed in such a manner that the contact body has, at least at the side facing the contact surface, an electrically-conductive surface as well as by electrodes, which are insulated from each other, being provided at the contact surfaces of the obstetric forceps. These electrodes are contactable with the contact body when the latter deforms in such a manner that with increasing deformation of the contact body, an increasing number of electrodes are interconnected by the electrically conductive surface of the contact body.

In this way, it can be prevented that the forceps presses the baby's head with so much force when the baby's head is grasped with the invented forceps that more pressure is applied at any locally confined point than the predetermined maximum pressure. The maximum pressure is set in such a manner that it is ensured that no injury to the baby's head can occur.

According to a preferred embodiment of the invented obstetric forceps, the contact body is made of a viscoplastic material and has a rounded cross section so that when pressure is applied on the contact body, the surface where the contact surfaces of the forceps blades touch the contact body is enlarged.

The contact bodies are preferably made of an electrically conductive material, at least in region of their surface area. The pressure detection device is provided with multiple electrodes that are electrically insulated from one another and run parallel in the longitudinal direction of the blades of the forceps. Upon deformation of the contact body, these electrodes are contactable with the contact body.

The invented preferred embodiment of the obstetric forceps is simple to realize and it can be determined with certainty if the maximum pressure has been reached at any locally confined deformation of the contact body.

The contact bodies can also be made of a thin-walled tube filled with a fluid. This type of contact body is particularly advantageous, because, due to the fluid, the contact body adapts to the shape of the baby's head in certain areas and the same pressure is applied at multiple points of contact between the contact bodies and the baby's head. The fluid thus leads to an isotropic distribution of pressure, with the maximum pressure not being reached until greater force is applied in operating the handles than in comparison to a contact body not filled with fluid, which leads to varying local pressure.

The fluid may be a liquid or a gas, in particular a compressed gas.

BRIEF DESCRIPTION OF THE DRAWINGS

The present invention is made more apparent in the following using preferred embodiments with reference to the accompanying drawings by way of example without the intention of limiting the overall inventive idea.

DESCRIPTION OF A PREFERRED EMBODIMENT, COMMERCIAL APPLICATION

Figure 1:
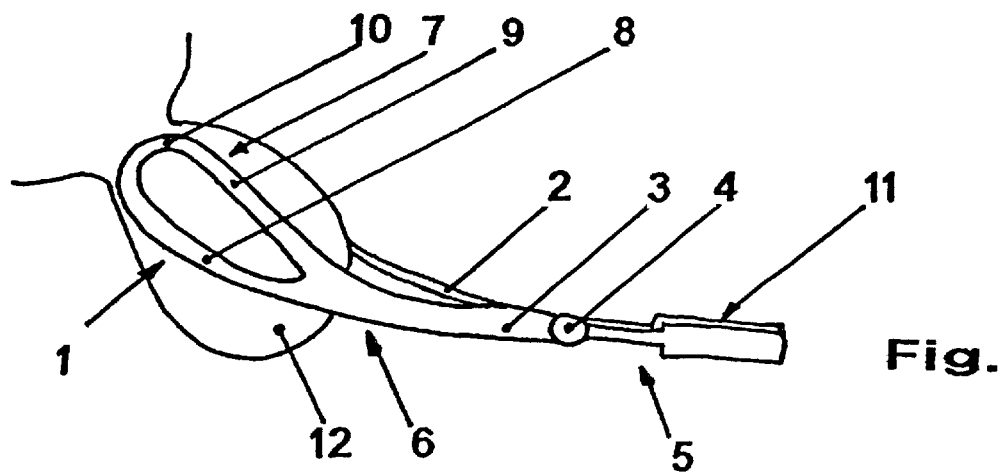
FIG. 1 shows a lateral view of an obstetric forceps grasping the head of a dummy.

The invented obstetric forceps 1 comprises two forceps elements 2, 3 which are moveably connected by means of a forceps joint 4, also referred to as the forceps catch. Obstetric forceps 1 is provided with a handle section 5 and a grasping section 6 which are separated by forceps joint 4. In grasping section 6, the forceps elements 2, 3 are each designed as the shape of a spoon 7 adapted to the shape of a baby's head. Spoon 7 comprises a lower forceps blade 8 and an upper forceps blade 9 as well as a rounded spoon tip (10).

Figure 2:
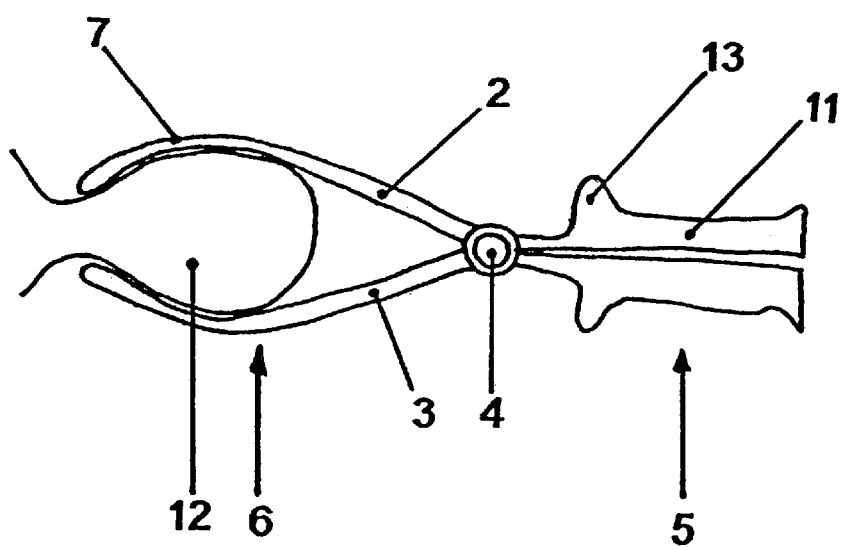
FIG. 2 shows a top view of the obstetric forceps and the head of the dummy.

At the handle section 5, the two forceps elements 2,3 are each provided with a handle 11 which are pressed together when grasping a baby's head 12 in order to apply pressure to it. A lateral projecting extraction hook 13 is provided at each of the end sections of handles 11 leading to the forceps joint 4. Force can be applied to these hooks 13 to extract the baby out of the mother's body (FIG. 2).

The parts of the forceps are made of a rigid material, such as e.g. metal or fiber reinforced plastic.

Figure 3:
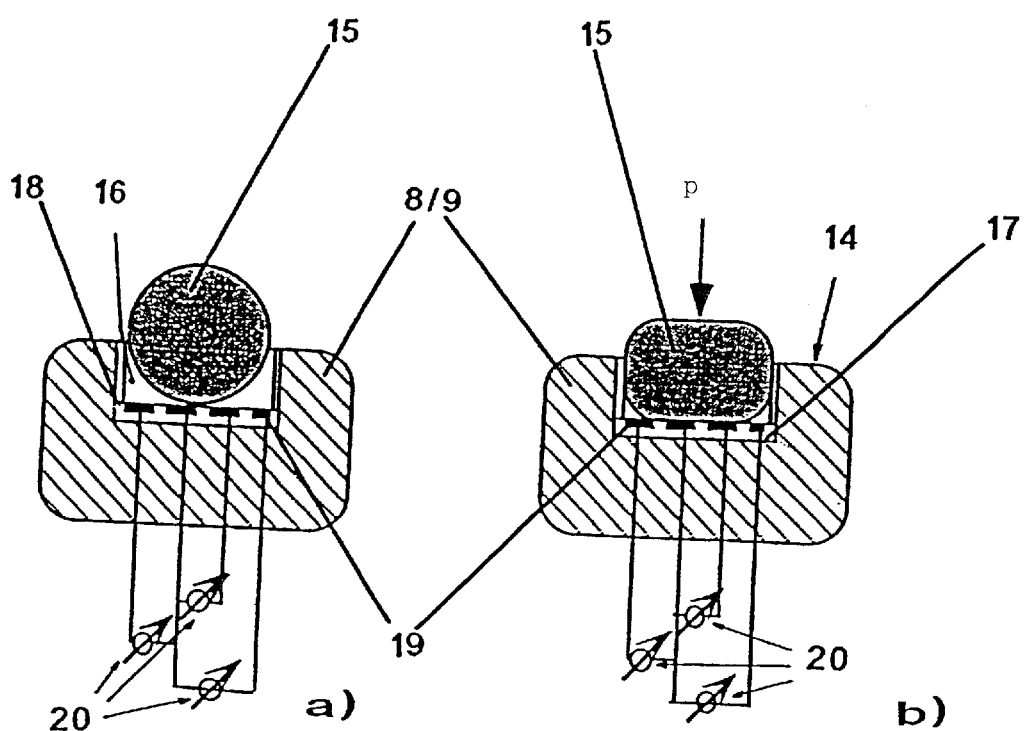
FIG. 3a shows a section through a blade of the invented forceps with a silicon rubber contact body in a no-load state
FIG. 3b shows the forceps blade of FIG. 3a in a loaded state.

FIGS. 3a and 3b both show a cross section of the invented preferred embodiment of the forceps blades.

At their contact surface 14 with which they come into contact with the baby's head 12, the forceps blades 8, 9 of an invented forceps 1 are provided with an elongated, elastically ductile contact body 15. In the preferred embodiment shown in FIGS. 3a and 3b, the contact body 15 is made of an electrically conductive silicon rubber. A groove 16 having a groove bottom 17 and groove walls 18 is provided in the contact surface of the forceps blades 8, 9. Electrically insulated electrodes 19 are provided running in the longitudinal direction of the forceps blades respectively the groove 16. Upon deformation of the electrically conductive contact bodies 15, these electrodes 19 are contacted with the same in such a manner that with increasing deformation of the contact body 15, an increasing number of electrodes 19 are interconnected by the electrically conductive contact body 15 (see FIG. 3b, according to which all the electrodes are interconnected via the contact body 15).

The electrodes 19 are electrically connected in pairs with electrical sensors 20, which, as in resistance measuring, determine whether pairs of the electrodes are electrically interconnected by means of the contact body 15. The more electrodes 19 are electrically interconnected by the contact body 15, the greater the force deforming the contact body 15 at the point of deformation. In the figures, the preferred embodiment is shown with only four electrodes. Fundamentally an embodiment with only two electrodes 19 suffices for the present invention. In order to differentiate the pressure force, it is useful to provide a multiplicity of electrodes disposed in parallel.

Contact body 15 of the preferred embodiment is made of a viscoplastic rubber material that is completely electrically conductive. In order to realize the present invention, however, it suffices if only the surface of the contact body 15 is electrically conductive.

In the event of multiple locally confined deformations at random points of the contact body 15, the invented contact body 15 and the arrangement of the electrodes 19 permit being able to detect if the maximum pressure has been exceeded at these points of deformation, because deformation at any point can already lead to an electrical connection between two electrodes 19 which is detectable by the sensors 20. The presence of such an electrical connection thus indicates having reached a maximum pressure and is translated into a signal that is recognizable by the obstetrician. For this purpose, for example an acoustical signal transmitter which generates a respective acoustical signal is provided.

Instead of an elastically ductile contact body 15 made of a viscoplastic rubber material, the contact body 15 can be made of a thin-walled tube 21. The tube is fillable with a fluid which may be a liquid or preferably a compressed gas.

If compressed gas is employed as the fluid, it is useful to provide on the obstetric forceps, integrated in the forceps, a pressure-resistant store tank (not shown) in which the compressed gas is stored. Before using the obstetric forceps, the store tank in the handle section is pumped up until a defined air pressure is reached. The tube at the forceps blades is first evacuated in such a manner that it lies flat against the blades of the forceps permitting easier entry of the forceps as the forceps spoon (each with a handle section) has to be introduced between the baby's head and the uterine cervix. For entry, a catch provided on the forceps is unlocked thereby permitting introduction of the two forceps spoons individually into the uterine cervix and placing them around the baby's head. Subsequently, the catch is relocked. Now the tube on the blades of the forceps can be connected to the store tank in the handle section by simply opening a valve so that pressure equalization occurs and the tube is inflated. Finally, extraction of the baby can start after possible fixing of the opening angle of the forceps, which is possible in some forceps.

Independent of the actual design of the preferred embodiment, it is essential for the present invention that a contact body 15 that is elastically ductile is provided at each forceps blade 8, 9 and a device for detecting a maximum pressure is provided at each contact body in such a manner that if there is one or multiple locally confined deformations at any point of the contact body, it can be detected whether the pressure causing the deformation is greater than the permitted maximum pressure.

LIST OF REFERENCE NUMBERS 1 obstetric forceps
2 forceps element
3 forceps element
4 forceps joint
5 handle section
6 grasping section
7 spoon
8 lower forceps blade
9 upper forceps blade
10 rounded spoon tip
11 handle
12 baby's head
13 extraction hook
14 contact surface
15 contact body
16 groove
17 groove bottom
18 groove wall
19 electrode
20 sensor

What is claimed is:

1. An obstetric forceps for grasping a baby during childbirth, said forceps having blades (8, 9) which are approximately adapted to the shape of a baby's head (12), are made of a rigid material and have contact surfaces (14) for grasping said baby's head (12), said contact surfaces (14) being provided with at least one device for detecting the pressure prevailing between said contact surface and said baby's head wherein said contact surfaces (14) of said forceps blades (8, 9) each are provided with an elongated, elastically ductile contact body (15), and said pressure detection device is designed in such a manner that said contact body has, at least at the side facing said contact surface, an electrically conductive surface and that electrodes (19), which are insulated from each other, are provided at said contact surfaces of said forceps blades, upon deformation of said contact body (15), said electrodes being contactable with the same in such a manner that with increasing deformation of said contact body (15), an increasing number of electrodes (19) are electrically interconnected by said electrically conductive surface of said contact body (15).

2. The obstetric forceps according to claim 1, wherein said contact bodies (15) are made of a viscoplastic material and having a rounded cross section.

3. The obstetric forceps according to claim 2, wherein said contact bodies (15) are made of an electrically conductive material at least in the region of their surface area and said electrodes insulated from one another run in parallel in the longitudinal direction of said forceps blades (8, 9).

4. The obstetric forceps according to claim 3, wherein grooves (16) having a groove bottom (17) and groove walls (18) are provided in said contact surfaces (14) of said forceps blades (8, 9), with said electrodes (19) being disposed on said groove bottom (17) and said contact bodies (15) projecting somewhat beyond said groove walls (18).

5. The obstetric forceps according to claim 1, wherein said contact bodies (15) are made of electrically conductive silicon rubber.

6. The obstetric forceps according to claim 2, wherein said contact bodies (15) have a circular cross section in a no-load state.

7. The obstetric forceps according to claim 1, wherein said contact bodies (15) each comprise a thin-walled tube (21) which is filled with a fluid (22).

8. The obstetric forceps according to claim 7, wherein said fluid (22) is a liquid.

9. The obstetric forceps according to claim 7, wherein said fluid (22) is a gas.

10. The obstetric forceps according to claim 9, wherein a pressure-resistant store tank from which compressed gas can be fed to said tube (21) is provided integrated in said obstetric forceps (1).

11. The obstetric forceps according to claim 10, wherein said tube (21) lies folded flat against said forceps blades (8, 9).

12. The obstetric forceps according to claim 1, wherein said forceps is provided with an electronic signal device which is electrically connected to the device for detecting a maximum pressure of multiple limited locally confined deformations of said contact body and is provided with a signal transmitter for generating a signal upon exceeding the maximum permissible pressure.

13. The obstetric forceps according to claim 12, wherein said signal transmitter is an acoustic signal transmitter.

* * * * *